(12) United States Patent
Bristow

(10) Patent No.: US 9,681,663 B2
(45) Date of Patent: Jun. 20, 2017

(54) METHOD FOR SPRAY TANK CLEANOUT

(71) Applicant: ROTAM AGROCHEM INTERNATIONAL COMPANY LIMITED, Chai Wan, Hong Kong (CN)

(72) Inventor: James Timothy Bristow, Chai Wan (CN)

(73) Assignee: ROTAM AGROCHEM INTERNATIONAL COMPANY LIMITED, Chai Wan (HK)

( * ) Notice: Subject to any disclaimer, the term of this patent is extended or adjusted under 35 U.S.C. 154(b) by 0 days.

(21) Appl. No.: 14/381,348

(22) PCT Filed: Mar. 26, 2013

(86) PCT No.: PCT/CN2013/073222
§ 371 (c)(1),
(2) Date: Aug. 27, 2014

(87) PCT Pub. No.: WO2013/155923
PCT Pub. Date: Oct. 24, 2013

(65) Prior Publication Data
US 2015/0065348 A1 Mar. 5, 2015

(30) Foreign Application Priority Data
Apr. 20, 2012 (GB) .................................. 1207097.5

(51) Int. Cl.
| A01N 43/40 | (2006.01) |
| A01N 43/64 | (2006.01) |
| A01N 43/60 | (2006.01) |
| A01N 43/46 | (2006.01) |
| A01N 43/66 | (2006.01) |
| A01N 43/54 | (2006.01) |
| A01N 43/48 | (2006.01) |
| A01N 47/36 | (2006.01) |

(52) U.S. Cl.
CPC .................................. *A01N 47/36* (2013.01)

(58) Field of Classification Search
None
See application file for complete search history.

(56) References Cited

U.S. PATENT DOCUMENTS

| 3,033,902 A | * | 5/1962 | Holland | ................ | C07C 311/54 |
| | | | | | 564/42 |
| 4,599,412 A | | 7/1986 | Sandell | | |
| 4,659,823 A | * | 4/1987 | Moore, Jr. | ........... | C07D 521/00 |
| | | | | | 504/178 |
| 5,658,855 A | * | 8/1997 | Nalewaja | ............... | A01N 33/08 |
| | | | | | 504/214 |
| 6,239,072 B1 | * | 5/2001 | Flint | ...................... | A01N 57/20 |
| | | | | | 504/127 |
| 8,932,988 B2 | * | 1/2015 | Parrish | ................... | A01N 25/30 |
| | | | | | 504/116.1 |
| 2007/0078057 A1 | | 4/2007 | Rowley | | |
| 2009/0325805 A1 | | 12/2009 | Parrish | | |

FOREIGN PATENT DOCUMENTS

| CN | 1077838 | A | | 11/1993 |
| CN | 1889831 | A | | 1/2007 |
| CN | 1889831 | | * | 3/2007 |
| CN | 101326917 | | * | 12/2008 |
| CN | 101352171 | A | | 1/2009 |
| CN | 101411331 | | * | 4/2009 |
| CN | 101507439 | A | | 8/2009 |
| CN | 102308798 | A | | 1/2012 |
| EP | 0124295 | | | 11/1984 |
| EP | 0304282 | | | 2/1989 |
| EP | 0375824 | | | 6/1990 |
| RU | 2290810 | C1 | | 1/2007 |
| RU | 2356228 | C2 | | 5/2009 |
| WO | 93/16596 | | | 9/1993 |
| WO | 9316596 | A1 | | 9/1993 |
| WO | 0049869 | | | 8/2000 |

OTHER PUBLICATIONS

International Search Report for PCT/CN2013/073222 dated Jul. 2009.
An English Language Translation of the International Search Report and Written Opinion, dated Jul. 11, 2013, issued in corresponding PCT application No. PCT/CN2013/073222.
An English Language Translation of an Office action, dated Aug. 26, 2014, issued in corresponding French Patent Application No. 1353475.
A certified English Language Translation of an office action, dated Jul. 1, 2015, issued in corresponding Chinese Application No. 2015062601229200; Patent No. 201210451087.5.

* cited by examiner

*Primary Examiner* — Alton Pryor
(74) *Attorney, Agent, or Firm* — Dickinson Wright PLLC

(57) ABSTRACT

A method for spray tank cleanout. In particular, the invention further relates to a method for reducing residual sulfonylurea pesticide contamination of a spray tank from which the sulfonylurea is applied, and a composition for achieving this method.

5 Claims, No Drawings

METHOD FOR SPRAY TANK CLEANOUT

This application is a 371 of PCT/CN2013/073222, filed 26 Mar. 2013, which claims benefit of GB 1207097.5, filed 20 Apr. 2012, the entire contents of which are incorporated herein by reference for all purposes.

BACKGROUND

Field

This present disclosure provides a method for spray tank cleanout. In particular, the disclosure further relates to a method for reducing residual sulfonylurea pesticide contamination of a spray tank from which the sulfonylurea is applied.

Description of Related Art

Sulfonylureas, as a class, are highly active pesticides. For this reason, it is desirable to clean out spray equipment before the equipment is subsequently used to treat crops sensitive to the sulfonamide herbicide used in the previous application. Adequate cleanout may require a rinsing procedure that is time-consuming and results in wastewater requiring proper environmental disposal. Furthermore, cleanout can be affected if the spray equipment contains organic deposits remaining from previous crop protection chemical applications or from other chemicals tank-mixed with the sulfonamide herbicide composition.

PCT patent application publication WO93/16596 describes a method for reducing residual sulfonylurea herbicide contamination of spray equipment by requiring as the first step the formulation of the sulfonylurea active ingredient in the form of an agriculturally suitable water soluble salt. The method for reducing residual sulfonylurea pesticide contamination of a spray tank from which the sulfonylurea is applied, comprising the steps: i) formulating the sulfonylurea the steps: agriculturally suitable water soluble salt composition before spray tank application, thereby increasing solubility of the sulfonylurea and decreasing the amount of insoluble sulfonylurea available for residual contamination of the spray tank; ii) applying the sulfonylurea salt composition to the crop while minimizing buildup of insoluble sulfonylurea in the spray tank; and (iii) rinsing the spray tank substantially free of residual sulfonylurea, after application, in an operation in which the sulfonylurea remaining in the spray tank is reduced significantly versus the amount remaining when sulfonylurea is not formulated as a water-soluble salt before application. But this method has disadvantages. In the tank cleanout protocol I, step 4, step 5, step 6, and step 7 all mentioned a cleaning solution. The cleaning solution can be water, or an ammonium hydroxide, or sodium hypochlorite solution. Especially in step 7, ammonium hydroxide solution was used. So even using sulfonylurea water soluble salt in the composition, washing the spray equipment with the cleaning solution was also necessary after finishing spraying.

SUMMARY

The present disclosure provided a composition with sulfonylurea which has improved spray equipment clean-out properties and reduces residual sulfonylurea herbicide contamination of spray equipment. There is no need for using a cleaning solution to wash the spray equipment after application. Simple washing with fresh water after application is enough. This facilitates the farmers' washing step and saves time.

An embodiment of the invention relates to a composition comprising:
(i) from 2% to 90% by weight sulfonylurea water soluble salt;
(ii) from 1% to 50% by weight ethanolamine;
(iii) from 0-95% of one or more additional formulating ingredients;
the sum of the weight percents of all the ingredients in the composition totaling 100%.

An embodiment of the invention further relates to a method for reducing residual sulfonylurea pesticide contamination of a spray tank from which the sulfonylurea is applied, comprising the steps:
(a) formulating the sulfonylurea as an agriculturally suitable water soluble salt;
(b) preparing a composition comprising by weight:
(i) from 2% to 90% sulfonylurea water soluble salt;
(ii) from 1% to 50% ethanolamine;
(iii) from 0-95% of one or more additional formulating ingredients;
the sum of the weight percents of all the ingredients in the composition totaling 100%;
(c) applying the sulfonylurea salt composition to the crop while minimizing buildup of insoluble sulfonylurea in the spray tank, and
(d) rinsing the spray tank substantially free of residual sulfonylurea, after application.

DETAILED DESCRIPTION OF SPECIFIC EMBODIMENTS

It has been discovered that the sulfonylureas herbicide composition according to an embodiment of the invention has improved spray equipment clean-out properties and reduces residual sulfonylurea herbicide contamination of spray equipment. In addition, there is no need for using a cleaning solution to wash the spray equipment after application. Simple washing with fresh water after application is enough. This facilitates the farmers' washing step and saves time.

The sulfonylureas whose spray tank buildup is curtailed by the method of an embodiment of this invention are the sulfonylurea acids either when used alone or with one or more tank mix partners. The benefits achieved by this invention have been found to be more pronounced when the sulfonylurea is employed with a tank mix partner. The benefits are even more noteworthy when earlier tank mixes have left organic deposits on inside spray tank surfaces. In such instances, it is believed that undissolved particles of the sulfonylurea are held by the organic deposit and kept from becoming resuspended or dissolved in the spray tank water. Thereafter, should the spray tank be employed on a crop sensitive to the sulfonylurea, damage may result either from migration into the tank water of particles formerly trapped by the organic deposit or by actual sloughing off of the organic deposit carrying embedded sulfonylurea particles with it.

The problem of difficult spray tank cleanout is exacerbated by sulfonylureas used at relatively high concentrates. Since water solubility of the sulfonylurea active ingredient in its acid form is so low, tank mixes of the sulfonylureas are primarily suspensions. Suspended particles can collect on tank walls, in tubing, or be trapped by organic deposits that may be present inside the tank. If a later tank mix sends the sulfonylurea into solution or suspension, sensitive crops can be damaged.

This problem is avoided partly by employing sulfonylureas in a water-soluble salt form. The sulfonylurea salt form shows a faster dissolution rate than the corresponding sulfonylurea acid. In order to avoid this problem completely, a washing with the clean solution is necessary after application.

The invention, in an embodiment, provides a composition comprising by weight:
(i) from 2% to 90% sulfonylurea water soluble salt;
(ii) from 1% to 50% ethanolamine;
(iii) from 0-95% of one or more additional formulating ingredients; the sum of all the ingredients in the composition totaling 100%.

The invention, in an embodiment, further provides a method for reducing residual sulfonylurea pesticide contamination of a spray tank from which the sulfonylurea is applied, comprising the steps:
(a) formulating the sulfonylurea as an agriculturally suitable water soluble salt;
(b) preparing a composition comprising by weight:
(i) from 2% to 90% sulfonylurea water soluble salt;
(ii) from 1% to 50% ethanolamine;
(iii) from 0-95% of one or more additional formulating ingredients;
the sum of all the ingredients in the composition totaling 100%;
(c) applying the sulfonylurea salt composition to the crop while minimizing buildup of insoluble sulfonylurea in the spray tank, and
(d) rinsing the spray tank substantially free of residual sulfonylurea after application.

The composition of the present invention has improved spray equipment clean-out properties and reduces residual sulfonylurea herbicide contamination of spray equipment. In addition, there is no need for using a cleaning solution to wash after application. Simple washing with fresh water after application is enough. This facilitates the farmers' washing step and saves time.

The sulfonylureas for use in the invention include:
2-chloro-N[[(4-methoxy-6-methyl-1,3,5-triazin-2-yl) amino]carbonyl]benzenesulfonamide (chlorsulfuron);
Methyl 2-[[[[(4,6-dimethyl-2-pyrimidinyl)amino]carbonyl] amino]sulfonyl]benzoate (sulfometuron-methyl);
Ethyl 2-[[[[[4-chloro-6-methoxy-2-pyrimidinyl]amino]carbonyl]amino]sulfonyl]benzoate (chlorimuron ethyl);
Methyl 2-[[[[(4-methoxy-6-methyl-1,3,5-triazin-2-yl) amino]carbonyl]amino]sulfonyl]benzoate (metsulfuron-methyl);
Methyl 2-[[[[[4,6-dimethoxy-2-pyrimidinyl]amino]carbonyl]amino]sulfonyl]-6(trifluoromethyl)-3-pyridine-carboxylate (flupyrsulfuron-methyl);
Methyl 2-[[[[[4-ethoxy-6-(methylamino)-1,3,5-triazin-2-yl] amino]carbonyl]amino]sulfonyl]benzoate (ethametsulfuron-methyl);
2-(2-chloroethyloxy)-N-[[(4-methoxy-6-methyl-1,3,5-triazin-2-yl)amino]carbonyl]-benzenesulfonamide;
Ethyl 5-[[[[(4,6-dimethoxy-2-pyrimidinyl)amino]carbonyl] amino]sulfonyl]-1-methyl-1H-pyrazole-4-carboxylate (pyrazosulfuron-ethyl);
N-[[(4,6-dimethoxy-2-pyrimidinyl)amino]carbonyl]-3-(ethylsulfonyl)-2-pyridinesulfonamide (rimsulfuron);
Methyl 3-[[[[(4-methoxy-6-methyl-1,3,5-triazine-2-yl) amino]carbonyl]amino]sulfonyl]-2-thiophenecarboxylate (thifensulfuron-methyl);
Methyl 2-[[[[N-(4-methoxy-6-methyl-1,3,5-triazine-2-yl)N-methylamino]carbonyl]amino]sulfonyl]benzoate (tribenuron-methyl);
Methyl 2-[[[[[(4,6-dimethoxy-2-pyrimidinyl)amino]carbonyl]amino]sulfonyl]methyl]benzoate (bensulfuron methyl);
2-[[[[[4,6-bis(difluoro methoxy)-2-pyrimidinyl]amino]carbonyl]amino]sulfonyl]benzoate;
2-[[[[(4,6-dimethoxy-2-pyrimidiny)amino]carbonyl]amino] sulfonyl]N,N-dimethyl-3-pyridinecarboxamide (nicosulfuron);
Methyl 2-[[[[[[4-dimethylamino]-6-(2,2,2-trifluoroethyoxy)-1,3,5-triazin-2-yl]amino]carbonyl]amino]sulfonyl]-3-methylbenzoate; and
N-[[(4,6-dimethyl-2-pyrimidinyl)amino]carbonyl]-1-methyl-4-(2-methy 1-2H-tetrazol-5-yl)-1H-pyrazole-5-sulfonamide (azimsulfuron).

More preferred sulfonylurea compounds are:
Methyl 3-[[[[(4-methoxy-6-methyl-1,3,5-triazine-2-yl) amino]carbonyl]amino]sulfonyl]-2-thiophenecarboxylate (thifensulfuron-methyl);
Methyl 2-[[[[(4,6-dimethyl-2-pyrimidinyl)amino]carbonyl] amino]sulfonyl]benzoate (sulfometuron-methyl);
Methyl 2-[[[[(4-methoxy-6-methyl-1,3,5-triazin-2-yl) amino]carbonyl]amino]sulfonyl]benzoate (metsulfuron-methyl);
Ethyl 5-[[[[(4,6-dimethoxy-2-pyrimidinyl)amino]carbonyl] amino]sulfonyl]-1-methyl-1H-pyrazole-4-carboxylate (pyrazosulfuron-ethyl);
N-[[(4,6-dimethoxy-2-pyrimidinyl)amino]carbonyl]-3-(ethylsulfonyl)-2-pyridinesulfonamide (rimsulfuron);
Methyl 2-[[N-(4-methoxy-6-methyl-1,3,5-triazine-2-yl)-N-methylamino]carbonyl]amino]sulfonyl]benzoate (tribenuron-methyl);
2-[[[[(4,6-dimethoxy-2-pyrimidiny)amino]carbonyl]amino] sulfonyl]N,N-dimethyl-3-pyridinecarboxamide (nicosulfuron);
2-chloro-N-[[(4-methoxy-6-methyl-1,3,5-triazin-2-yl) amino]carbonyl]benzenesulfonamide (chlorsulfuron)

Salts of the sulfonylureas are generally known as are methods for making them. Preferred salt cations are the sodium, potassium, calcium, magnesium, ammonium and alkylammonium cations. Preferred sulfonylurea salts are the sodium and calcium salts of tribenuron methyl; the potassium salt of thifensulfuron methyl; the ammonium salt of chlorsulfuron and the potassium salt of metsulfuron methyl.

In the composition of an embodiment of the invention, the amount of ethanolamine present may present depend upon the concentrate of the sulfonylurea water soluble salt active ingredient and may be determined by routine experimentation. The ethanolamine is preferably present in an amount such as to give a weight ratio of the sulfonylurea water soluble salt to the ethanolamine of from 1:90 to 90:1.

The composition of embodiments of the present invention may be provided in the form of liquid or solid. Use formulations include dusts, granules, pellets, solutions, suspensions, emulsions, gels, actives in plastic, wettable powders, emulsion concentrates, dry flowables and the like, consistent with the physical properties of the active ingredient, mode of application and environmental factors such as soil type, moisture and temperature. Sprayable formulations can be extended in suitable media and used at spray volumes from about one to several hundred liters per hectare. High strength compositions are primarily used as intermediates for further formulation.

The composition of embodiments of the present invention can contain one or more additional formulating ingredients in a total amount by weight of 0 to 95%. Additional formulating ingredients can include liquid diluents, solid diluents, wetting agents, dispersants, emulsifiers, chemical stabilizers and other formulation ingredients.

Liquid diluents include, for example water, N,N-dimethylamide, dimethyl sulfoxide, N-alkylpyrrolidone, ethylene glycol, polypropylene glycol, propylene carbonate, dibasic esters, paraffines, alkylbenzenes, alkyl naphthalenes, glycerine, triacetine, oils of olive, castor, linseed, sesame, corn, peanut, cotton-seed, soybean, rape-seed and coconut, ketones such as cyclohexanone, 2-heptanone, isophorone and 4-hydroxy-4-methyl-2-pentanone, acetates such as hexyl acetate, heptyl acetate and octyl acetate, and alcohols such methanol, cyclohexanol, decanol, benzyl and tetrahydrofurfuryl alcohol.

Solid diluents can be water-soluble or water-insoluble. Water-soluble solid diluents include salts such as alkali metal phosphates (e.g., sodium dihydrogen phosphate), alkaline earth phosphates, sulfates of sodium, potassium, magnesium and zinc, sodium and potassium chloride, and sodium benzoate and sugars and sugar derivatives such as sorbitol, lactose and sucrose. Examples of water-insoluble solid diluents include, but are not limited to clays, synthetic and diatomaceous silicas, calcium and magnesium silicates, titanium dioxide, aluminum, calcium and zinc oxide, calcium and magnesium carbonate, calcium and barium sulfate, and charcoal.

The emulsifiers can be cationic, anionic or nonionic, but are more typically anionic or nonionic. Examples of particularly suitable anionic surfactants for this purpose are sulfonates such as calcium dodecyl benzesulfonate. Examples of particularly suitable nonionic surfactants are polyoxyethylated (POE) sorbitan esters such as POE(20) sorbitan trioleate and polyoxyethylated (POE) sorbitol esters such as POE(40) sorbitol hexaoleate. POE(20) sorbitan trioleate is commercially available under the tradenames ATLAS G1086 and CIRRASOL G1086 marketed by UniqEMA. Combination of a POE sorbitan ester with a POE sorbitol ester allows optimizing the HLB (hydrophiliclipophilic balance) value of the surfactant to obtain the highest quality emulsion (smallest suspended droplets) when the composition is added to water. High quality of emulsions typically leads to optimal herbicidal performance.

Wetting agents include but are not limited to alkyl sulfosuccinates, laureates, alkyl sulfate and phosphate esters, acetylenic diols, ethoxyfluorinated alcohols, ethoxylated silicones, alkyl phenol ethoxylates, benzene sulfonates, alkyl-substituted benzene sulfonates, alkyl α-olefin sulfonates, naphthalene sulfonates, alkyl-substituted naphthalene sulfonates, condensates of naphthalene sulfonates and alkyl-substituted naphthalene sulfonates with formaldehyde, and alcohol ethoxylates. Of note are compositions comprising up to 10% by weight of wetting agent.

Dispersants include, but are not limited to, sodium, calcium and ammonium salts of ligninsulfonates (optionally polyethoxylated); sodium and ammonium salts of maleic anhydride copolymers; sodium salts of condensed phenolsulfonic acid; and naphthalene sulfonate-formaldehyde condensates. Of note are compositions comprising up to 10% by weight of dispersant. Ligninsulfonates, such as sodium ligninsulfonates, are particularly useful for the composition of embodiments of the invention.

Chemical stabilizers prevent decomposition of active ingredient during storage. Inorganic bases such as lithium, sodium and potassium phosphates can help prevent decomposition of active ingredient. Chemical stabilizers include, but are not limited to lithium, sodium, and potassium phosphates, sodium dihydrogen phosphate, sulfates of alkaline earth metals and transition metals such as magnesium, zinc, aluminum and iron; calcium chloride and oxide; and boric anhydride. Of note are compositions comprising up to 10% by weight of chemical stabilizer.

Other formulation ingredients can be used in embodiments of the present invention, such as dyes, defoamers, drying agents, and the like. These ingredients are known to one skilled in the art.

Solutions are prepared by simply mixing the ingredients. Fine solid compositions are made by blending and, usually, grinding as in a hammer mill or fluid energy mill. Water-dispersible granules can be produced by agglomerating a fine powder composition; suspensions are prepared by wet-milling; granules and pellets can be made by spraying the active ingredient upon preformed granular carriers or by agglomeration techniques. Pellets can be prepared as described in U.S. Pat. No. 4,172,714. Water-dispersible and water-soluble granules can also be prepared as taught in DE3246493.

Sulfonylurea salts of this invention can be used alone or in combination with other commercial herbicides (including other sulfonylureas or sulfonylurea salts), insecticides, or fungicides. Mixtures containing sulfonylurea and other commercial herbicides, insecticides, or fungicides with ethanolamine are particularly useful in minimizing spray tank cleanout when compared to the same mixture without ethanolamine In the following examples, all percentages are by weight and all formulations are worked up in conventional ways.

PREPARATION EXAMPLES

Examples

Example 1

| Thifensulfuon methyl potassium salt | 1% |
|---|---|
| Ethanolamine | 90% |
| Sorbitan trioleate (Uniqema Tween 85) | 5% |
| Calcium dodecyl benzesulfonate (Clariant 70B) | 3% |
| Water | balance to 100% |

Example 2

High Strength Concentrate

| Metsulfuron-methyl sodium salt | 90% |
|---|---|
| Ethanolamine | 1% |
| Silica aerogel | 0.5% |
| Synthetic amorphous fine silica | balance to 100% |

Example 3

Wettable Power

| Pyrazosulfuron-ethyl sodium salt | 20% |
|---|---|
| Ethanolamine | 10% |
| Sodium alkyl naphthalenesulfoate (Morwet EFW, Akzo Nobel) | 3% |
| Sodium ligninsulfonates (Polyfon H, Westvaco) | 3% |
| Clay | balance to 100% |

Example 4

Water Dispersible Granule

| | |
|---|---|
| Tribenuron methyl sodium salt | 75% |
| Ethanolamine | 15% |
| Sodium alkyl naphthalenesulfoate (Morwet EFW, Akzo Nobel) | 2% |
| Sodium ligninsulfonate (Polyfon H, Westvaco) | 3% |
| Clay | balance to 100% |

Example 5

Suspensions

| | |
|---|---|
| Mesosulfuron methyl calcium salt | 20% |
| Ethanolamine | 20% |
| Sodium ligninsulfonate (Polyfon H, Westvaco) | 5% |
| Sorbitan trioleate (Uniqema Tween 85) | 5% |
| PG | 5% |
| Water | balance to 100% |

Example 6

Soluble Granules

| | |
|---|---|
| Metsulfuron methyl potassium salt | 50% |
| Ethanolamine | 30% |
| Sodium alkyl naphthalenesulfoate (Morwet EFW, Akzo Nobel) | 2% |
| Sodium ligninsulfonate (Polyfon H, Westvaco) | 3% |
| Sucrose | balance to 100% |

Example 7

Soluble Powder

| | |
|---|---|
| Chlorsulfuron ammonium salt | 5% |
| Ethanolamine | 15% |
| Sodium alkyl naphthalenesulfoate (Morwet EFW, Akzo Nobel) | 2% |
| Sodium ligninsulfonate (Polyfon H, Westvaco) | 3% |
| Sucrose | balance to 100% |

Example 8

Solutions

| | |
|---|---|
| Rimsulfuron sodium salt | 2% |
| Ethanolamine | 80% |
| Sorbitan trioleate (Uniqema Tween 85) | 5% |
| Calcium dodecyl benzesulfonate (Clariant 70B) | 3% |
| Water | balance to 100% |

Example 9

Suspensions

| | |
|---|---|
| Trifluoxyfluron calcium salt | 4% |
| Ethanolamine | 80% |
| Sodium ligninsulfonate (Polyfon H, Westvaco) | 5% |
| Sorbitan trioleate (Uniqema Tween 85) | 5% |
| PG | 5% |
| Water | balance to 100% |

Example 10

Water Dispersible Granule

| | |
|---|---|
| Sulfometuron methyl magnesium salt | 40% |
| Ethanolamine | 2% |
| Sodium alkyl naphthalenesulfoate (Morwet EFW, Akzo Nobel) | 2% |
| Sodium ligninsulfonate (Polyfon H, Westvaco) | 3% |
| Clay | balance to 100% |

Example 11

Granules

| | |
|---|---|
| Bensulfuron-methyl ammonium salt | 10% |
| Ethanolamine | 20% |
| Attapulgite granules | balance to 100% |

Example 12

Wettable Powders

| | |
|---|---|
| Nicosulfuron calcium salt | 75% |
| Ethanolamine | 15% |
| Sodium alkyl naphthalenesulfoate (Morwet EFW, Akzo Nobel) | 3% |
| Sodium ligninsulfonate (Polyfon H, Westvaco) | 3% |
| Clay | balance to 100% |

Example 13

Solutions

| | |
|---|---|
| Triflusulfuron-methyl sodium salt | 15% |
| Ethanolamine | 50% |
| Sorbitan trioleate (Uniqema Tween 85) | 5% |
| Calcium dodecyl benzesulfonate (Clariant 70B) | 3% |
| N-methylpyrrolidone | balance to 100% |

Example 14

Solutions

| | |
|---|---|
| Chlorsulfuron ammonium salt | 2% |
| Ethanolamine | 60% |
| Sorbitan trioleate (Uniqema Tween 85) | 5% |
| Calcium dodecyl benzesulfonate (Clariant 70B) | 3% |
| Water | balance to 100% |

Example 15

Soluble Powders

| | |
|---|---|
| Ethamesulfuron-methyl sodium salt | 60% |
| Ethanolamine | 2% |
| Sodium alkyl naphthalenesulfoate (Morwet EFW, Akzo Nobel) | 2% |
| Sodium ligninsulfonate (Polyfon H, Westvaco) | 3% |
| Sucrose | balance to 100% |

Example 16

Soluble Granules

| | |
|---|---|
| Azimsulfuron potassium salt | 50% |
| Ethanolamine | 1% |
| Sodium alkyl naphthalenesulfoate (Morwet EFW, Akzo Nobel) | 2% |
| Sodium ligninsulfonate (Polyfon H, Westvaco) | 3% |
| Sucrose | balance to 100% |

Example 17

Suspensions

| | |
|---|---|
| Chlorimuron-ethyl calcium salt | 1% |
| Ethanolamine | 50% |
| Sodium ligninsulfonate (Polyfon H, Westvaco) | 5% |
| Sorbitan trioleate (Uniqema Tween 85) | 5% |
| PG | 5% |
| Water | balance to 100% |

Example 18

Soluble Granules

| | |
|---|---|
| Flupyrsulfuron-methyl sodium salt | 50% |
| Ethanolamine | 5% |
| Sodium alkyl naphthalenesulfoate | 2% |
| Sodium ligninsulfonate (Polyfon H, Westvaco) | 3% |
| Sucrose | balance to 100% |

Example 19

Suspensions

| | |
|---|---|
| Flupyrsulfuron-methyl calcium salt | 5% |
| Ethanolamine | 50% |
| Sodium ligninsulfonate (Polyfon H, Westvaco) | 5% |
| Sorbitan trioleate (Uniqema Tween 85) | 5% |
| PG | 5% |
| Water | balance to 100% |

COMPARATIVE EXAMPLES

In Comparative examples A-S without using Ethanolamine, the other ingredients are the same as with the corresponding Examples 1-19, and ethanolamine was replaced using diluents in the composition.

The compositions were evaluated by the following clean-out test procedure that determines the sulfonamide herbicide residue that could potentially remain in organic deposits in a spray tank.

Tank Cleanout Protocol I
(Sulfonylurea Plus Tank Mix Partner)

Step 1

Add water to the tank and when half-filled, add a sample from Example 1-19 and Comparative example A-S in each separate tank with agitation. Fill tank to the 90% level with water. Agitate the tank for a minimum of 5 to 10 minutes.

Step 2

Spray the tank contents through the boom. Drain any remainder from the tank.

Step 3

Rinse the interior tank surfaces with water; use about 10% of the tank capacity. Spray this rinse through the boom. Drain the remainder from the tank.

Step 4

Remove all nozzles, nozzle screens, in-line filters, or filters of any type and clean thoroughly in a bucket of water. Remove any residues or deposits using a brush.

Step 5

Fill tank half full with fresh water. Sample water wash in tank (sample used for bioassay test). Spray 10 to 20 gallons through the boom and then the sample at a nozzle (sample used for bioassay test). Drain the remainder of the contents. Remark: In whole cleaning process, only fresh water was used. Additional cleaning solution or ammonium hydroxide is not used.

TABLE I

| Examples | Sulfonylurea | Initial Sulfonylurea concentration in the tank mix (ppm) | Tank mix partner | Percent injury[1] |
|---|---|---|---|---|
| Example 1 | Thifensulfuon methyl potassium salt | 400 | 2,4-D | 0 |

TABLE I-continued

| Examples | Sulfonylurea | Initial Sulfonylurea concentration in the tank mix (ppm) | Tank mix partner | Percent injury[1] |
|---|---|---|---|---|
| Comparative example A | Thifensulfuon methyl potassium salt | 400 | 2,4-D | 50 |
| Example 2 | Metsulfuron-methyl sodium salt | 500 | Propiconazole | 0 |
| Comparative example B | Metsulfuron-methyl sodium salt | 500 | propiconazole | 90 |
| Example 3 | Pyrazosulfuron-ethyl sodium salt | 750 | Flutriafol | 0 |
| Comparative example C | Metsulfuron methyl sodium salt | 750 | Flutriafol | 20 |
| Example 4 | Tribenuron methyl sodium salt | 600 | 2,4-D | 0 |
| Comparative example D | Tribenuron methyl sodium salt | 600 | 2,4-D | 40 |
| Example 5 | Mesosulfuron methyl calcium salt | 775 | propiconazole | 0 |
| Comparative example E | Tribenuron methyl calcium salt | 775 | propiconazole | 90 |
| Example 6 | Metsulfuron methyl potassium salt | 500 | MCPA | 0 |
| Comparative example F | Metsulfuron methyl potassium salt | 500 | MCPA | 0 |
| Example 7 | Chlorsulfuron ammonium salt | 660 | Propiconazole | 20 |
| Comparative example G | Chlorsulfuron ammonium salt | 660 | Propiconazole | 90 |
| Example 8 | Rimsulfuron sodium salt | 700 | 2,4-D | 0 |
| Comparative example H | Rimsulfuron sodium salt | 700 | 2,4-D | 60 |
| Example 9 | Trifluoxyfluron calcium salt | 1150 | Propiconazole | 0 |
| Comparative example I | Rimsulfuron calcium salt | 1150 | Propiconazole | 30 |
| Example 10 | Sulfometuron methyl magnesium | 700 | MCPA | 0 |
| Comparative example J | Sulfometuron methyl magnesium | 700 | MCPA | 40 |
| Example 11 | Bensulfuron-methyl ammonium salt | 660 | 2,4-D | 0 |
| Comparative example K | Bensulfuron-methyl ammonium salt | 660 | 2,4-D | 80 |
| Example 12 | Nicosulfuron calcium salt | 720 | Propiconazole | 0 |
| Comparative example L | Nicosulfuron calcium salt | 720 | Propiconazole | 60 |
| Example 13 | Triflusulfuron-methyl sodium salt | 280 | 2,4-D | 10 |
| Comparative example M | Triflusulfuron-methyl sodium salt | 280 | 2,4-D | 60 |
| Example 14 | Chlorsulfuron ammonium salt | 570 | Propiconazole | 0 |
| Comparative example N | Chlorsulfuron ammonium salt | 570 | Propiconazole | 70 |
| Example 15 | Ethametsulfuron-methyl sodium salt | 400 | MCPA | 10 |
| Comparative example O | Ethametsulfuron-methyl sodium salt | 400 | MCPA | 60 |
| Example 16 | Azimsulfuron potassium salt | 835 | 2,4-D | 20 |
| Comparative example P | Azimsulfuron potassium salt | 835 | 2,4-D | 90 |
| Example 17 | Chlorimuron-ethyl calcium salt | 430 | Propiconazole | 0 |
| Comparative example Q | Chlorimuron-ethyl calcium salt | 430 | Propiconazole | 80 |
| Example 18 | Flupyrsulfuron-methyl sodium salt | 380 | Flutriafol | 0 |
| Comparative example R | Flupyrsulfuron-methyl sodium salt | 380 | Flutriafol | 0 |
| Example 19 | Flupyrsulfuron-methyl calcium salt | 190 | MCPA | 0 |
| Comparative example S | Flupyrsulfuron-methyl calcium salt | 190 | MCPA | 10 |

Percent injury[1]: injury to greenhouse sugarbeets after sprayed with final fresh water from the tank cleanout procedure.

The data summarized in Table I (using Protocol I) show that the compositions of Example 1-19 according to embodiments of the present invention plus tank mix partner has a failure rate of 0. The comparative example A-S plus tank mix partner suffered a failure rate of about 79%. (Note: Test failure corresponds to a greenhouse result of >20% injury to sugarbeets in the bioassay test).

These results show that simple cleaning with fresh water after application of the compositions according to embodiments of the present invention plus tank mix partner is successful without using additional cleaning solution or ammonium hydroxide in the whole process of cleaning. However the simple cleaning with fresh water after application of the corresponding sulfonylurea salt plus tank partner without Ethanolamine is a failure without using additional cleaning solution or ammonium hydroxide in the whole process of cleaning.

Tank Cleanout Protocol II (Sulfonylurea with No Tank Partner)

Step 1

Divide the Example 1-19 and Comparative example A-S to be tested into 2 equal portions. Prepare a concentrated slurry with one portion, and a paste with the other portion. Spread and/or spray the paste and slurry onto the tank interior and let sit overnight. This procedure produces dried deposits on the tank surfaces to simulate worse-case field conditions.

Step 2

Rinse the tank interior with clean water, using a volume of 10-20% of the tank capacity, allowing the rinse to flush through the boom and hoses.

Step 3:

Fill the tank with clean water and agitate for 10 minutes. Discard the water, flushing at least 10-20% through the boom and nozzles.

Step 4

Remove any nozzles, nozzle screens and in-line filters and clean with fresh water.

Step 5

Rinse the tank with clean water, using a volume of 10-20% of the tank capacity. Allow the rinse water to accumulate in the tank and then discard through the boom and nozzles. Drain any remaining rinse water from the tank.

Step 6

Fill the tank half full with water Sample water wash in tank (sample used for bioassay test). Spray 10 to 20 gallons through the boom and then sample at a nozzle (sample used for bioassay test). Drain the remainder of the contents.

Remark: In whole cleaning process, only fresh water was used. Additional cleaning solution or ammonium hydroxide is not used.

TABLE II

| Examples | Sulfonylurea | Initial Sulfonylurea concentrate in the tank (ppm) | Percent injury[1] |
|---|---|---|---|
| Example 1 | Thifensulfuon methyl potassium salt | 400 | 0 |
| Comparative example A | Thifensulfuon methyl potassium salt | 400 | 50 |
| Example 2 | Metsulfuron-methyl sodium salt | 500 | 0 |
| Comparative example B | Metsulfuron-methyl sodium salt | 500 | 60 |
| Example 3 | Pyrazosulfuron-ethyl sodium salt | 750 | 0 |
| Comparative example C | Metsulfuron methyl sodium salt | 750 | 10 |
| Example 4 | Tribenuron methyl sodium salt | 600 | 0 |
| Comparative example D | Tribenuron methyl sodium salt | 600 | 20 |
| Example 5 | Mesosulfuron methyl calcium salt | 775 | 0 |
| Comparative example E | Tribenuron methyl calcium salt | 775 | 85 |
| Example 6 | Metsulfuron methyl potassium salt | 500 | 0 |
| Comparative example F | Metsulfuron methyl potassium salt | 500 | 20 |
| Example 7 | Chlorsulfuron ammonium salt | 660 | 10 |
| Comparative example G | Chlorsulfuron ammonium salt | 660 | 70 |
| Example 8 | Rimsulfuron sodium salt | 700 | 0 |
| Comparative example H | Rimsulfuron sodium salt | 700 | 50 |
| Example 9 | Trifluoxyfluron calcium salt | 1150 | 0 |
| Comparative example I | Rimsulfuron calcium salt | 1150 | 20 |
| Example 10 | Sulfometuron methyl magnesium | 700 | 0 |
| Comparative example J | Sulfometuron methyl magnesium | 700 | 20 |
| Example 11 | Bensulfuron-methyl ammonium salt | 660 | 0 |
| Comparative example K | Bensulfuron-methyl ammonium salt | 660 | 50 |
| Example 12 | Nicosulfuron calcium salt | 720 | 0 |
| Comparative example L | Nicosulfuron calcium salt | 720 | 50 |
| Example 13 | Triflusulfuron-methyl sodium salt | 280 | 0 |
| Comparative example M | Triflusulfuron-methyl sodium salt | 280 | 70 |
| Example 14 | Chlorsulfuron ammonium salt | 570 | 0 |
| Comparative example N | Chlorsulfuron ammonium salt | 570 | 60 |
| Example 15 | Ethametsulfuron-methyl sodium salt | 400 | 10 |
| Comparative example O | Ethametsulfuron-methyl sodium salt | 400 | 20 |
| Example 16 | Azimsulfuron Potassium salt | 835 | 0 |
| Comparative example P | Azimsulfuron potassium salt | 835 | 85 |
| Example 17 | Chlorimuron-ethyl calcium salt | 430 | 0 |
| Comparative example Q | Chlorimuron-ethyl calcium salt | 430 | 75 |
| Example 18 | Flupyrsulfuron-methyl sodium salt | 380 | 0 |
| Comparative example R | Flupyrsulfuron-methyl sodium salt | 380 | 20 |
| Example 19 | Flupyrsulfuron-methyl calcium salt | 190 | 0 |
| Comparative example S | Flupyrsulfuron-methyl calcium salt | 190 | 50 |

Percent injury[1]: injury to greenhouse sugarbeets after sprayed with final fresh water from the tank cleanout procedure.

The data summarized in Table II (using Protocol II) show that the compositions of Example 1-19 according to embodiments of the present invention in the absence of a tank partner has a failure rate of 0. The comparative example A-S in the absence of a tank mix partner suffered a failure rate of about 63%. (Note: Test failure corresponds to a greenhouse result of ≥20% injury to sugarbeets in the bioassay test).

The results show that simple cleaning with fresh water after application of the compositions according to embodiments of the present invention in the absence of a tank mix partner is successful without using additional cleaning solution or ammonium hydroxide in the whole process of cleaning. However the simple cleaning with fresh water after application of the corresponding sulfonylurea salt in the absence of a tank mix partner without Ethanolamine is a failure without using additional cleaning solution or ammonium hydroxide in the whole process of cleaning.

Bioassay Protocol

The bioassay protocol employed to determine the percent injury of the crop (sugarbeets) sprayed with the final rinse solution after tank cleanout is described herein. Sugarbeet seedlings (at the two-leaf stage) were grown in the greenhouse (14 hour photoperiod at 21° C. with light and 10 hours at 17° C. in the dark) and sprayed with unmodified samples of effluent from various sprayer cleanout procedures. An automatic belt sprayer was used, and the samples were applied at a rate of approximately 45 gal/A. Three replicate pots, with four sugarbeet plants/pot, were treated with each sample. The sprayer was rinsed 12 times between each sample to ensure that there would not be carryover between samples.

Plants were held in the greenhouse until they were evaluated, 14 to 23 days after treatment. Injury of treated plants was assessed visually on a scale of 0 to 100 (0=injury, 100=complete kill) compared to control plants. Injury ratings were based on the presence of various symptoms including reduced biomass, stunting, inhibited development, chlorosis, necrosis, leaf spotting, and leaf puckering or deformation.

The invention claimed is:

1. A composition comprising by weight:

(i) from 2% to 90% of a herbicidal sulfonylurea water soluble salt, wherein the sulfonylurea is selected from the group consisting of amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flupyrsulfuron-methyl, flazasulfuron, flucetosulfuron, foramsulfuron, halosulfuron-methyl, imazosulfuron, iodosulfuron-methyl, mesosulfuron-methyl, metsulfuron-methyl, oxasulfuron, primisulfuron-methyl, prosulfuron, pyrazosulfuron-ethyl, rimsulfuron, sulfometuron-methyl, sulfosulfuron, thifensulfuron-methyl, triasulfuron, triflusulfuron-methyl, and tritosulfuron;

(ii) from 1% to 50% ethanolamine, wherein the composition having ethanolamine improves spray equipment clean-out and reduces residual sulfonylurea herbicide contamination left in the spray material in comparison to the composition without the ethanolamine;

(iii) from 0-95% of one or more additional formulating ingredients;

a sum of all the ingredients in the composition totaling 100%; and wherein a weight ratio of the sulfonylurea water soluble salt to the ethanolamine is from 1:90 to 90:1.

2. The composition of claim 1, wherein the sulfonylurea is selected from the group consisting of:

metsulfuron-methyl, sulfometuron-methyl, rimsulfuron, thifensulfuron-methyl, chlorsulfuron, flupyrsulfuron-methyl, pyrazosulfuron-ethyl, ethametsulfuron-methyl, bensulfuron methyl, mesosulfuron-methyl, chlorimuron-ethyl, azimsulfuron, and triflusulfuron-methyl.

3. A method for reducing residual sulfonylurea pesticide contamination of a spray tank from which the sulfonylurea is applied, comprising the steps:

(a) formulating the sulfonylurea as an agriculturally suitable water soluble salt;

(b) preparing a composition comprising by weight:

from 2% to 90% sulfonylurea water soluble salt, wherein the sulfonylurea is selected from the group consisting of amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flupyrsulfuron-methyl, flazasulfuron, flucetosulfuron, foramsulfuron, halosulfuron-methyl, imazosulfuron, iodosulfuron-methyl, mesosulfuron-methyl, metsulfuron-methyl, oxasulfuron, primisulfuron-methyl, prosulfuron, pyrazosulfuron-ethyl, rimsulfuron, sulfometuron-methyl, sulfosulfuron, thifensulfuron-methyl, triasulfuron, triflusulfuron-methyl, and tritosulfuron;

(ii) from 1% to 50% ethanolamine, wherein the composition having ethanolamine improves spray equipment clean-out and reduces residual sulfonylurea herbicide contamination left in the spray material in comparison to the composition without the ethanolamine;

(iii) from 0-95% of one or more additional formulating ingredients;

a sum of all the ingredients in the composition totaling 100%; and wherein a weight ratio of the sulfonylurea water soluble salt to the ethanolamine is from 1:90 to 90:1;

(c) applying the sulfonylurea salt composition to a crop while minimizing buildup of insoluble sulfonylurea in the spray tank, and (d) rinsing the spray tank substantially free of the residual sulfonylurea after application.

4. The method of claim 3, wherein the sulfonylurea salt is employed in the absence of a tank mix partner.

5. The method of claim 3, wherein the sulfonylurea salt is employed in the presence of a tank mix partner.

* * * * *